(12) United States Patent
Nagasaki et al.

(10) Patent No.: US 7,410,699 B2
(45) Date of Patent: Aug. 12, 2008

(54) FINELY PARTICULATE COMPOSITE CONTAINING CARBON COMPOUND ENCAPSULATED IN A POLYMER MICELLE OF A BLOCK COPOLYMER

(75) Inventors: Yukio Nagasaki, Moriya (JP); Kazunori Kataoka, Tokyo (JP); Ryosuke Kodaka, Kanazawa (JP)

(73) Assignee: Japan Science and Technology Agency, Saitama (JP)

( * ) Notice: Subject to any disclaimer, the term of this patent is extended or adjusted under 35 U.S.C. 154(b) by 41 days.

(21) Appl. No.: 10/575,549

(22) PCT Filed: Sep. 6, 2004

(86) PCT No.: PCT/JP2004/013255

§ 371 (c)(1),
(2), (4) Date: Apr. 10, 2006

(87) PCT Pub. No.: WO2005/035651

PCT Pub. Date: Apr. 21, 2005

(65) Prior Publication Data

US 2007/0077432 A1    Apr. 5, 2007

(30) Foreign Application Priority Data

Oct. 10, 2003 (JP) ............................. 2003-352666
Feb. 10, 2004 (JP) ............................. 2004-033696

(51) Int. Cl.
*B32B 5/16* (2006.01)
*B01J 13/02* (2006.01)

(52) U.S. Cl. .................. 428/407; 427/213.36; 427/216; 427/221

(58) Field of Classification Search ................. 428/407; 427/213.36, 216
See application file for complete search history.

(56) References Cited

U.S. PATENT DOCUMENTS

| | | | |
|---|---|---|---|
| 6,881,484 B2 * | 4/2005 | Kataoka et al. | 428/407 |
| 7,122,133 B2 * | 10/2006 | Kataoka et al. | 252/514 |
| 7,138,490 B2 * | 11/2006 | Nakanishi et al. | 530/345 |
| 7,264,876 B2 * | 9/2007 | Smalley et al. | 428/407 |
| 2001/0041801 A1 * | 11/2001 | Friedman et al. | 548/217 |
| 2004/0068207 A1 | 4/2004 | Tabata | |
| 2006/0093885 A1 * | 5/2006 | Krusic et al. | 429/33 |
| 2006/0251896 A1 * | 11/2006 | Ferencz et al. | 428/407 |

FOREIGN PATENT DOCUMENTS

| | | |
|---|---|---|
| JP | 9-235235 | 9/1997 |
| JP | 2002-241307 | 8/2002 |
| JP | 2003-147418 | 5/2003 |

* cited by examiner

*Primary Examiner*—H. T Le
(74) *Attorney, Agent, or Firm*—Wenderoth, Lind & Ponack, L.L.P.

(57) ABSTRACT

This invention provides a finely particulate composite wherein a fine particle of block copolymer having a poly(ethyleneglycol) chain segment and a poly(meth)acrylate ester chain segment containing, on its side chain, a tertiary amino group and/or a secondary amino group has, encapsulated therein, a carbon compound, e.g., fullerene or carbon nanotube which may contains, encapsulated therein, a metal. This composite is water-soluble, and is usable as an active oxygen scavenger. This composite, when it has a metal encapsulated therein, is usable as a contrast medium.

15 Claims, 4 Drawing Sheets

FINELY PARTICULATE COMPOSITE CONTAINING CARBON COMPOUND ENCAPSULATED IN A POLYMER MICELLE OF A BLOCK COPOLYMER

TECHNICAL FIELD

This invention relates to a finely particulate composite wherein a carbon compound of closed-shell structure, except graphite and diamond, having 30 to 2000 carbon atoms is encapsulated in a block copolymer-originated structure (or polymer micelle), and to a finely particulate composite wherein an ultrafine metal particle is encapsulated in the fine particle, and also to the use of such a composite.

BACKGROUND ART

Fullerene and carbon nanotube which have a closed-shell structure and which are composed of carbon atoms alone are, owing to their novel structure, expected to be usable in the wide range of technical field such as medicine, internal diagnosis, cosmetics, etc.

Fullerene is, however, water-insoluble, and, therefore, there has been a certain limitation on the use of fullerene in these technical fields. Thus, with a view to solubilizing fullerene, there have been provided various kinds of fullerol wherein hydroxyl group is introduced into carbon atoms of fullerene (e.g., Japanese Patent Application Laid-Open Publication No. Hei 7-048302). In the case of metal-encapsulating fullerene, there have also been presented those whose surface is covered with polysaccharides having a functional group selected from the group consisting of sulfone group, ketone group, amino group and alkyl group (e.g., Japanese Patent Application Laid-Open Publication No. Hei 7-048302).

Furthermore, it has been reported that, when fullerene is added to an aqueous solution of fluoroalkyl chain-terminated acryloylmorpholine oligomer or N,N-dimethylacrylamide oligomer or the like with sufficient stirring, there are given self-organized materials (self-assembly) wherein the amount of solubilized fullerene is 100 μg/ml (see Journal of Colloid and Interface Science, 263, (2003), 1-3). It is further known that a charge transfer complex which has been prepared with use of the electron acceptability of fullerene (e.g., fullerene $C_{60}$) or a $C_{60}$-containing polymer which has been prepared by grafting fullerene with hydrophilic polymer such as poly (ethylene glycol), poly(vinyl pyrrolidone) and poly[(dimethylamino)ethyl-methacrylate] gives a solubilized fullerene. Moreover, $C_{60}$-b-poly[(dimethylamino)ethylmethacrylate] has been provided, and its physical properties have been studied (Dai et al., Langmuir 2004, PAGE EST: 6. 8 A-G). It is suggested that this block polymer forms in an aqueous solvent a micelle having fullerene as a core and polymer as a shell, and is thus solubilized.

DISCLOSURE OF INVENTION

As stated above, conventional techniques have succeeded to some extent in solubilizing fullerene. According to Journal of Colloid and Interface Science, 263, (2003), 1-3, for instance, the stirring of fullerene and the above-mentioned oligomer at room temperature for about five days gave a self-organized material which showed an improved water-solubility of about 100 μg/ml whereas fullerene had usually a water-solubility of 21.0 μg/ml. Thus improved solubility is however still unsatisfactory for fullerene to be used in technical field such as medicine, internal diagnosis, cosmetics, etc. $C_{60}$-containing polymer, on the other hand, also improves the water-solubility of fullerene. It is however not easy to prepare $C_{60}$-containing polymer. Thus, the purpose of this invention is to provide a stable aqueous solution or dispersion which comprise fullerene, a fine particle which contains, encapsulated therein, fullerene which shows a higher solubility in water, and a process to easily produce them and also the use thereof.

K. Kataoka et al., Macromolecules 1999, 32, 6892-6894, whose authors partially overlap with the authors of the present invention, provided a polymer micelle composite of DNA and polyethylene glycol-block-poly(2-(N,N-dimethylamino)ethylmethacrylate as a powerful means for the delivery of DNA or the like to a target in a living body. The inventors of the present invention, on the other hand, have found that $C_{60}$-fullerene which is quite different in physical properties and structure from anionically-charged DNA or the like forms a composite with block copolymer such as polyethylene glycol-block-poly(2-(N,N-dimethylamino)ethylmethacrylate in an aqueous solution, and that said fullerene is thereby effectively solubilized. Furthermore, it has been confirmed that a composite which is formed by such an improved solubilizing method shows a water-solubility higher than that of those produced by conventional process, and can be held stable at a high concentration in a state of an aqueous solution.

It has also been confirmed that such an improved solubilizing method provides a fine particulate composite of not only $C_{60}$-fullerene but also of a wide range of carbon compounds of closed-shell structure having 30 to 2000, preferably 60 to 120, carbon atoms, or of even carbon compounds which contain ultrafine metal particles encapsulated therein, which shows a high water-solubility and which can exist stable in an aqueous medium. It has further been confirmed that a structure of block copolymer which contains said carbon compound alone encapsulated therein has a strong active oxygen-scavenging effect in an aqueous medium, and that said structure can be used widely and conveniently in fields such as food, medicine and cosmetics.

Thus, this invention provides a finely particulate composite wherein a carbon compound of closed-shell structure which essentially consists of 30 to 2000 carbon atoms is covered with polymer chain, which is characterized in that said carbon compound is encapsulated in a structure which is originated in a block copolymer having a polymer chain segment containing a recurring unit which has, on its side chain, a tertiary amino group and/or a secondary amino group and a poly (ethyleneglycol) chain segment, and which has the former segment as a core and the latter segment as a shell.

As another embodiment, this invention provides a process to produce the above-mentioned finely particulate composite which process is characterized in that a carbon compound of closed-shell structure which essentially consists of 30 to 2000 carbon atoms and a block copolymer having a polymer chain segment containing a recurring unit which has, on its side chain, a tertiary amino group and/or a secondary amino group and a poly(ethyleneglycol) chain segment are dissolved in a dipolar aprotic solvent and mixed, and that the resulting mixture is dialyzed against an aqueous solvent through a dialysis membrane whose molecular weight cut off is 12000 to 14000, to give finely particulate composite wherein said carbon compound is encapsulated in a structure originated in the block copolymer.

As another embodiment, this invention provides also an active oxygen scavenger which contains the above-mentioned finely particulate composite as an effective ingredient.

As another embodiment, this invention provides a finely particulate composite wherein a carbon compound of closed-shell structure which essentially consists of 30 to 2000 carbon atoms is covered with polymer chain, which is characterized in that said carbon compound is encapsulated in a structure which is originated in a block copolymer having a polymer chain segment containing a recurring unit which has, on its side chain, a tertiary amino group and/or a secondary amino group and a poly(ethyleneglycol) chain segment, and which has the former segment as a core and the latter segment as a shell, and that an ultrafine particle of metal either in the form of metal element or in the form of its ion is encapsulated in the closed-shell structure of said carbon compound.

The finely particulate composite of this invention, even in the form of powder which is prepared by freeze-drying after produced, is very easily dissolved or dispersed in water at a high concentration. Thus, this invention also provides a powdery matter which gives a transparent or uniform, and stable solution.

BEST MODE FOR CARRYING OUT THE INVENTION

Figure 1:
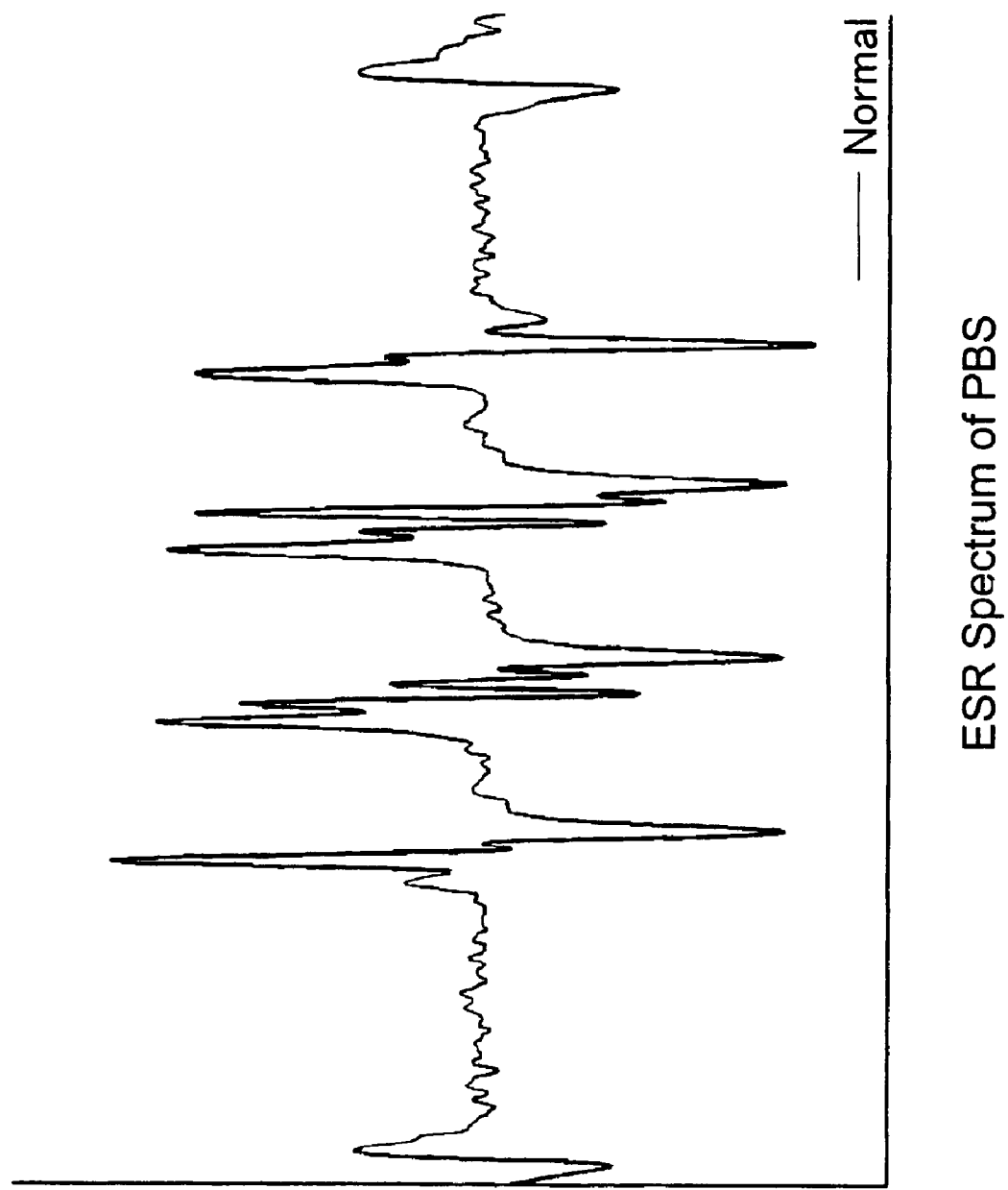
FIG. 1 is an ESR spectrogram of PBS.

The phrase "essentially consists of . . . carbon atoms" in this invention means that, beside carbon atoms, there may be contained hydroxyl group, oxo group, or the like in an amount of 10% or less, preferably 5% or less, more desirably 1% or less, based on the number of carbon atoms so long as the purpose of this invention is achieved. Especially desirable carbon compound in this invention is, however, carbon compound which is composed of carbon atoms alone. The term "closed-shell structure", on the other hand, means not only known structure which fullerene and carbon nanotube can take, but also a net structure which is packed tight with carbon atoms and a net structure which may be curved in one or two directions, for instance the one which is disclosed in the pamphlet of WO 93/15768. In consideration of the use of this invention, however, the carbon compound of this invention preferably has a so-called football-like structure; in particular there can be mentioned known $C_{60}$, $C_{84}$, $C_{32}$, $C_{50}$, $C_{66}$, $C_{70}$, $C_{76}$, $C_{78}$, $C_{90}$, $C_{96}$ and $C_{120}$ fullerenes as preferable examples.

Block copolymer which can form a structure (or polymer micelle) which contains such a carbon compound encapsulated therein may be of any molecular species provided that it has a polymer segment containing a recurring unit which has, on its side chain, a tertiary amino group and/or a secondary amino group and a poly(ethyleneglycol)-originated segment as a hydrophilic segment, and that it achieves the purpose of this invention, for example, to solubilize $C_{30}$-$C_{120}$ fullerene or carbon nanotube of up to $C_{2000}$ in water effectively.

Preferably, however, the block copolymer of this invention has a segment originated from a monomer of general formula (A) as follows:

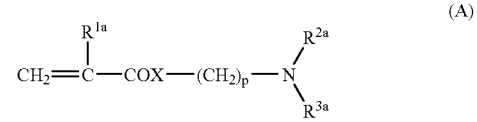

(A)

wherein $R^{1a}$ denotes a hydrogen atom or a $C_{1-6}$ alkyl group, $R^{2a}$ and $R^{3a}$ either, independently, denote a $C_{1-6}$ alkyl group or, taken together, may form, with the nitrogen atom to which they are bound, a five- or six-membered heterocycle which may contain further one or two nitrogen atoms, an oxygen atom or a sulfur atom, X denotes —O— or —NH—, and p denotes an integer of 2 to 6.

With regard to alkyl group and the like in the above-mentioned definition, $C_{1-6}$ alkyl group means a straight or branched alkyl group having 1 to six carbon atoms, examples of which include methyl, ethyl, n-propyl, isopropyl, n-butyl, sec-butyl, tert-butyl, n-pentyl and n-hexyl. Examples of five- or six-membered heterocycle which $R^{2a}$ and $R^{3a}$, taken together, form with the nitrogen atom to which they are bound include the following:

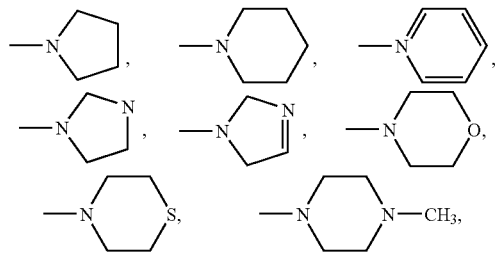

In order that the above-mentioned hydrophilic polymer chain segment and polymer chain segment containing a recurring unit which has, on its side chain, a tertiary amino group and/or a secondary amino group may be incorporated as segments in a block copolymer to be used in this invention, both polymers are previously prepared, and are then bound to each other by any binding means that is known in the art. In another method to provide a block copolymer to be used in this invention, a polymer which corresponds to one of segments is prepared, and, at one terminal of the polymer, a monomer which corresponds to the other segment is polymerized and grown. As a typical example of such a method, although not restrictive, there can be mentioned a method which is disclosed in the above-mentioned Kataoka et al., and block copolymer obtained in such a method, which has general formula (A-1) as follows:

(A-1)

$$H\text{-}(CCH_2)_m\text{-}(OCH_2CH_2)_n\text{-}O\text{-}L\text{-}Y$$

with side groups: $R^1$, $C=O$, $X'$, $(CH_2)_{p'}$, $N$, $R^2$, $R^3$ wherein $R^1$ denotes a hydrogen atom or a $C_{1-6}$ alkyl group, $R^2$ and $R^3$ either, independently, denote a $C_{1-6}$ alkyl group or, taken together, may form, with the nitrogen atom to which they are bound, a five- or six-membered heterocycle which may contain further one or two nitrogen atoms, an oxygen atom or a sulfur atom, X' denotes —O— or —NW—, p' denotes an integer of 2 to 6, L denotes a $C_{1-6}$ alkylene or a valence bond, Y denotes a hydrogen atom, a hydroxyl group, a carboxyl group, an amino group, an acetalized formyl group or a formyl (or aldehyde) group, m denotes an integer of 1 to 10,000, n denotes an integer of 10 to 20,000, and p' denotes an integer of 2 to 6, is conveniently used in this invention.

A structure (or polymer micelle) which contains a carbon compound encapsulated therein means a material in which the surface of said carbon compound is fully covered with such a block copolymer as mentioned above so that the carbon compound may be solubilized in water. Although not restrictive, such a structure is preferably a molecular assembly of block copolymer molecules which have been associated with each other in an aqueous medium, so that a polymer chain segment of the block copolymer containing a recurring unit which has, on its side chain, a tertiary amino group and/or a secondary amino group may constitute an internal core or central part to encapsulate the carbon compound therein as a core, and that a poly(ethyleneglycol) chain segment may cover the exterior part (such a molecular assembly is sometimes referred to as polymer micelle in this specification). In the above and the other part of this specification, aqueous medium may mean water, a mixture solution of water and an organic solvent miscible with water (e.g., ethanol, acetone, N,N-dimethylformamide (DMF), dimethylsulfoxide (DMSO), acetonitrile, etc.), and a solution which contains water or said mixture solution and, optionally, buffer solution and/or osmotic pressure regulator.

Although not theoretically restricted, highly water-soluble poly(ethyleneglycol) chain segment in the above structure has a very high mobility in aqueous medium, and is therefore capable of covering the surface of the structure in a brush-like manner. It is understood that, on this account, the whole of the structure can be solubilized in water to a good extent even when water-insoluble carbon compound is encapsulated in the structure.

A finely particulate composite which comprises such a structure can be obtained by a method which is employed in usual preparation of polymer micelle, e.g., by adding fullerene to an aqueous solution of block copolymer and stirring for a long period of time, or by dissolving carbon compound and block copolymer in a solvent such as methylene chloride or the like which can dissolve both of them, thereafter distilling off the solvent, and subsequently gradually dissolving residual matter in water. However, finely particulate composite which contains carbon compound such as fullerene encapsulated therein which is produced by the above-mentioned methods has, in most cases, had only a limited water-solubility (e.g., about 100 μg/ml or less).

Further studying these preparation methods, the inventors of this invention have confirmed that a finely particulate composite which is obtained by dissolving carbon compound such as fullerene and block copolymer in a dipolar aprotic solvent and dialyzing the resulting solution which method is generally regarded as inferior in the efficiency of polymer micelle-formation has significantly higher water-solubility (e.g., about 500 μg/ml or more, in detail, about 1 μg/ml to about 4 μg/ml) than composites which are obtained by the above-mentioned methods. Thus, this invention also provides a process to produce a finely particulate composite, as another embodiment of this invention.

Any kind of dipolar aprotic solvent is usable in the production method of this invention so long as it gives such a high solubility as mentioned above. Preferably, however, DMF and DMSO can be mentioned. Firstly, carbon compound such as fullerene and block copolymer are dissolved in such a solvent. As for the order of dissolving, carbon compound and block copolymer may be dissolved either in this order, or in reverse order, or at the same time. In dissolving, solvent may be heated to boiling point if necessary, or may be used at room temperature. In dissolving or mixing, solution may be subjected to sonication. Thus obtained solution is left to stand still for a certain time (several hours to one night) after insoluble matters are filtrated out where necessary. Thereafter, the solution is dialyzed against water or preferably distilled water through a dialysis membrane having a desired molecular weight cut off. Dialysis is usually conducted for two hours at least three times against water about more than 10 times the amount of solution to be treated. Finally, dialysis is carried out overnight. Dialysis membrane has preferably a molecular weight cut off of 12000-14000. Furthermore, dialysis membrane is fully swollen with distilled water before used. The above-mentioned operation may be conducted at room temperature. If necessary, however, it may be carried out under cooling (e.g., 0 to 5° C.) or under heating (40 to 80° C.). In this manner, there is efficiently obtained a finely particulate composite containing carbon compound encapsulated in polymer micelle, which has a solubility of, for instance, 500 μg/ml or more in distilled water at 25° C. The concentration of carbon compound and block copolymer in the mixture is not limited so long as they are dissolved in solvent used. Usually, however, carbon compound is preferably used at a proportion of 0.001 wt % to 10 wt % per volume of solution, and block copolymer is preferably used at a proportion of 0.001 wt % to 2 wt % per volume of solution.

Such a finely particulate composite containing only carbon compound encapsulated therein is encapsulated in a structure of block copolymer. Even though only carbon compound is encapsulated, the composite shows a strong active oxygen-scavenging action in aqueous medium. Hence, the above-mentioned finely particulate composite is usable as an active oxygen-scavenger in environment, in particular inside or outside a living body, wherein active oxygen has bad influence. In detail, it can be employed in a field where organic or inorganic anti-oxidant or superoxide dismutase (SOD) and the like are advantageously usable, e.g., as an agent to inhibit oxidation-deterioration of fat of foods, anti-aging skin care cosmetics, cancerocidal medicine, etc.

Even when a composite which encapsulates ultrafine metal particle in place of carbon compound is used, the above-mentioned method to produce finely particulate composite as an embodiment of this invention provides a solution of composite with a high solubility in water or a uniform dispersion which holds the composite stable in an aqueous medium.

Thus, this invention also provides as another embodiment a finely particulate composite which is characterized by containing an ultrafine particle of metal either in the form of metal element or in the form of its ion encapsulated in the closed-shell structure of said carbon compound. As such a metal, any species is usable so long as it is employed in fields wherein the utility of metal is improved if the metal is solubilized in aqueous medium, e.g., fields of medical treatment, diagnosis and foods. Thus, metals which are used as a contrast medium for the medical examination or diagnosis of diseases or injuries of some organ of living body, e.g., paramagnetic metals originated in elements selected from the group consisting of gadolinium (Gd), europium (Eu), terbium (Tb) and erbium (Er), and metals originated in elements which are capable of providing oxides such as zinc, copper, magnesium, iron, platinum, etc. These metals can also take the form of ion. Moreover, these metals can be encapsulated in carbon compound, in the form of ultrafine particle. Ultrafine particle typically means one of a size which is capable of being encapsulated in the above-mentioned fullerene or carbon nanotube. A part of such fullerenes which contain metal encapsulated therein are available in the market, and are usable as they are. Such a fullerene as mentioned above is also obtained by evaporating oxide of desired metal with laser, together with graphite, under high temperature and high pressure by any know method, e.g., by the method as mentioned in the above-mentioned Japanese Patent Application Laid-Open (KOKAI) No. Hei 8-143478.

Incidentally, examples of block copolymer concerning a finely particulate composite which is characterized by containing an ultrafine particle of metal either in the form of metal element or in the form of its ion encapsulated in the closed-shell structure of carbon compound are in common with those of block copolymer of the above-mentioned composite which contains carbon compound alone encapsulated therein.

Thus prepared finely particulate composite wherein paramagnetic metal element-encapsulating carbon compound is encapsulated in a structure (or polymer micelle) formed by block copolymer can be kept stable at a high concentration in an aqueous medium, and is therefore usable as a contrast medium to be administered into blood vessel.

In the following, this invention is further detailedly explained with concrete examples, which are not intended to restrict this invention.

EXAMPLE OF PRODUCTION OF BLOCK COPOLYMER

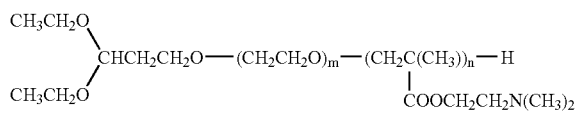

Structural formula of acetal–PEG/PAMA

A 200 ml egg-shaped flask was filled, in an argon atmosphere, with 50 ml of distilled tetrahydrofuran (THF) as a solvent, and further with 157 μl of 3,3'-diethoxy-1-propanol (Mw=148, d=0.941) as an initiator, which was metallized by the subsequent addition of 2.73 ml of potassium naphthalene (K-Naph (c=0.3656 mol/l)).

Thereafter, 5.68 ml of ethyleneoxide (EO (Mw=44, d=0.88)) was put in the same flask, and, then, the resulting mixture was stirred for two days under cooling with water. After two days, s small amount was sampled for GPC analysis, and, then, 4.29 ml of 2-(N,N-dimethylamino)ethylmethacrylate (PAMA; MW=157.21) was put in the same flask, and, then, the resulting mixture was stirred for 30 minutes under cooling with ice. Subsequently, GPC sampling was conducted, and, finally, reaction was stopped with methanol.

After the reaction was stopped, reaction liquid was re-precipitated with isopropyl alcohol, centrifuged, and was then freeze-dried with benzene, and, thus, reaction product was recovered.

Purified polymer had a molecular weight of PEG/PMAMA=4,500/5,500.

COMPOSITE PRODUCTION EXAMPLE 1

Dispersion-stabilization of Fullerene in Water by Dialysis Method

In 25 ml of dimethylformamide (DMF) as a solvent, 1 mg of $C_{60}$ fullerene and 13.8 mg of acetal-PEG-PMAMA block copolymer (PEG/PAMA=4,500/5,500) were added (in the case where F:P=1:1), so that the mixing ratio of fullerene to polymer (F:P) might be 1:0, 1:0.5, and 1:1, and, then, the resulting solution was sonicated for six hours, and was then left to stand still overnight. Then, the solution was put in a dialysis membrane with a molecular weight cut off of 12000 to 14000 which had been swollen with distilled water overnight, and was thus dialyzed (water was replaced three times). Solvent was removed by freeze-drying from thus obtained 30 ml solution of fullerene-encapsulating fine particles. Subsequently, 5 ml of distilled water was added for the sake of re-dispersion. Then, DLS measurement was conducted again.

Thus obtained concentrated solution showed black brown color which was characteristic of fullerene. The composite of this invention was quite readily dispersed and dissolved in water even after freeze-drying, whereas, in the absence of block copolymer, concentrating would have caused turbidity. Solutions having a mixing ratio F:P of 1:1 and 1:0.5 were subjected again to DLS measurement. It was found that, even though photon count had increased as compared with the time before the solution was concentrated and re-dispersed, sufficient photon count was not able to be obtained as compared with the values previously obtained. It is guessed that fullerene particles which were prepared under the above-mentioned condition had been dispersed with a particle size not larger than the one (about 3 nm) which is detectable by light scattering, or, in other words, had been dispersed nearly in the form of molecular dispersion.

COMPOSITE PRODUCTION EXAMPLE 2

Dispersion-stabilization of $C_{60}$ Fullerene in Water by Bubbling Evaporation Method With 25 ml of methylene chloride as a solvent, 1 mg of fullerene was mixed, and was dissolved therein by sonication. Thereafter, 139 mg of acetal-PEG-PMAMA block copolymer (PEG/PAMA=4,500/5,500) was added to the solvent. After sonicated for two hours, the resultant solution was left to stand still overnight.

Thus prepared methylene chloride solution was added dropwise to 40 ml of distilled water which was being subjected to argon bubbling. Thus prepared solution, like the one of the above Production Example 1, provided finely particulate composite which gave a pale yellow transparent solution. The obtained solution of fullerene composite which was dispersion-stabilized in water was subjected to DLS measurement. It was confirmed that nanoparticles having a particle size of about 170 nm had been formed.

COMPOSITE PRODUCTION EXAMPLE 3

Example of Production of Aqueous Solution of High-concentration Fullerene

With 150 ml of DMF solution, 100 mg of $C_{60}$ fullerene was mixed at room temperature, and the resulting solution was sonicated for three hours. Then, materials insoluble in solvent were filtrated out by using a 0.45 μm hydrophobic filter (manufactured by Millipore Corporation). Subsequently, acetal-PEG-PMAMA block copolymer (PEG/PAMA=5,000/5,900) was added, so that the concentration of polymer might be 5 mg/ml with regard to the solvent, and, then, the resulting solution was left to stand still overnight. Then, the solution was put in a bag made of dialysis membrane with a molecular weight cut off of 12000 to 14000 which had been swollen with distilled water overnight, and was thus dialyzed against 2 l of solution (DMF: distilled water=150:2000) (water was replaced five times, i.e., after 2, 4, 6, 8 and 10 hours; recovered after 24 hours).

Thereafter, thus dialyzed solution was freeze-dried to give powder. A sample of the powder was re-dissolved with 400 μl of distilled water, and was subjected to UV-Vis spectrum measurement, and, thus, solubility was calculated from the absorbance of fullerene. It was found that fullerene had been solubilized in water at a concentration as high as 2.9 mg/ml.

Confirmation of Active Oxygen-scavenging Action of Fullerene-encapsulating Finely Particulate Composite A vessel was filled with 30 μl of 5,5-dimethyl-1-pyrroline N-oxide (DMPO), which is a spin-trapping agent, which had been diluted to ½ concentration with Milli-Q ultrapure water, 50 μl of 5 mM hypoxanthine (HPX) which had been adjusted with 100 mM Milli-Q ultrapure water-adjusted phosphate buffer solution, 20 μl of 9.625 mM diethylenetriamine-N,N,N',N'',N''-pentaacetic acid (DTPA), 50 μl of a sample (1. PBS, 2. fullerene solution) and 50 ml of 0.4 U/ml xanthine oxidase (XOD) in order. Ninety seconds after the addition of XOD, spectrum measurement was conducted with ESR.

Figure 2:
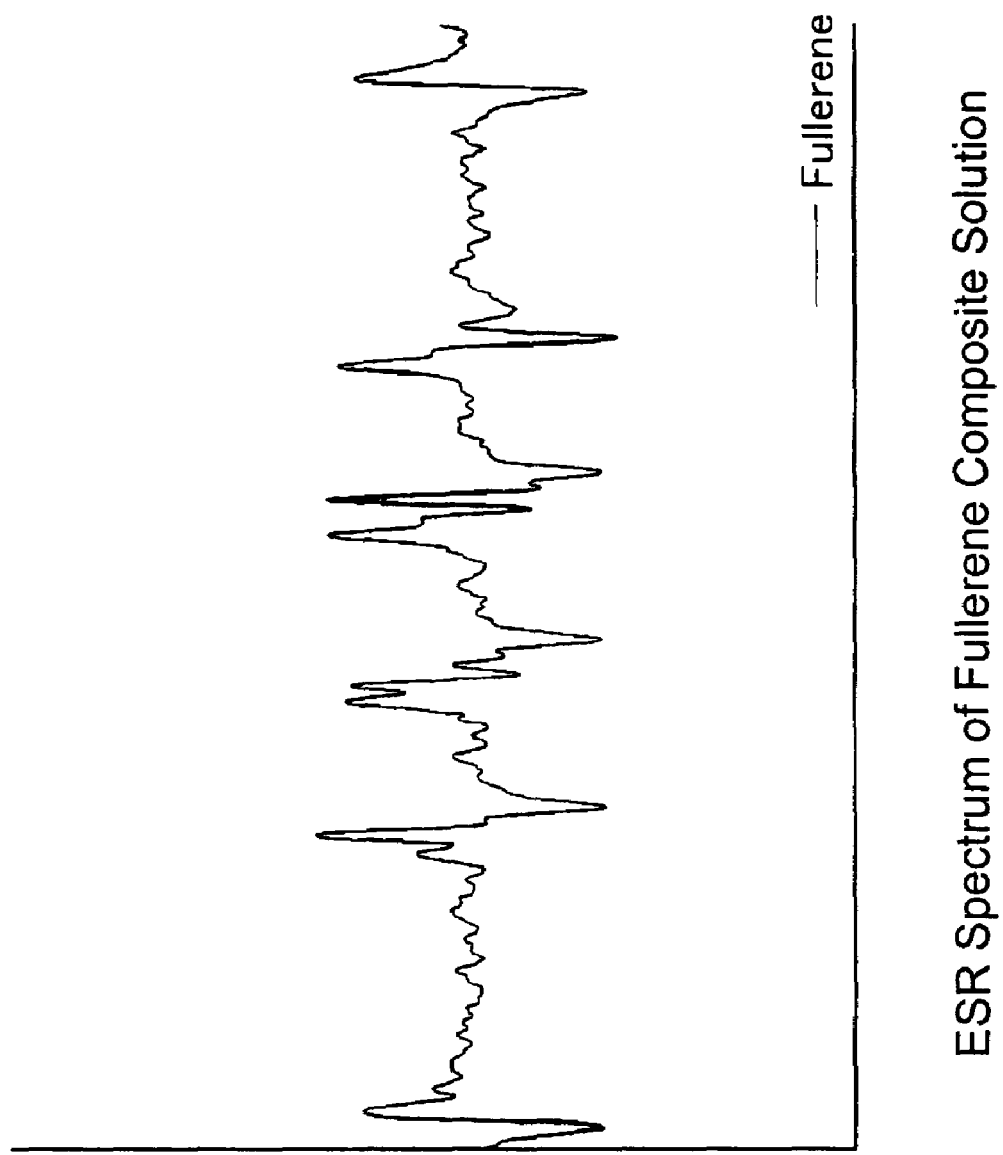
FIG. 2 is an ESR spectrogram of an aqueous solution of the fullerene composite of this invention.

Measurement conditions for ESR spectrum method were as follows: Power: 9 mW; Central magnetic field: 339.9 mT; Sweep width: ±5 mT; Modulation width: 79 μT; Sweep time: One minute; Amplification: 630; Time constant: 0.1 second FIG. 1 and FIG. 2 show respectively ESR spectrograms of samples, i.e., PBS and solution of fine particles of fullerene encapsulated in polymer micelle of acetal-PEG-PMAMA block copolymer (PEG/PMAMA=5,000/5,900). These spectrums were integrated, and were compared with each other with regard to their areas, and, thus, their active hydrogen-inhibiting effects were compared with each other. When the area of sample of PBS which had no active hydrogen-inhibiting effect was supposed to be 100%, the area of solution of fine particles was about 30%.

Figure 3:
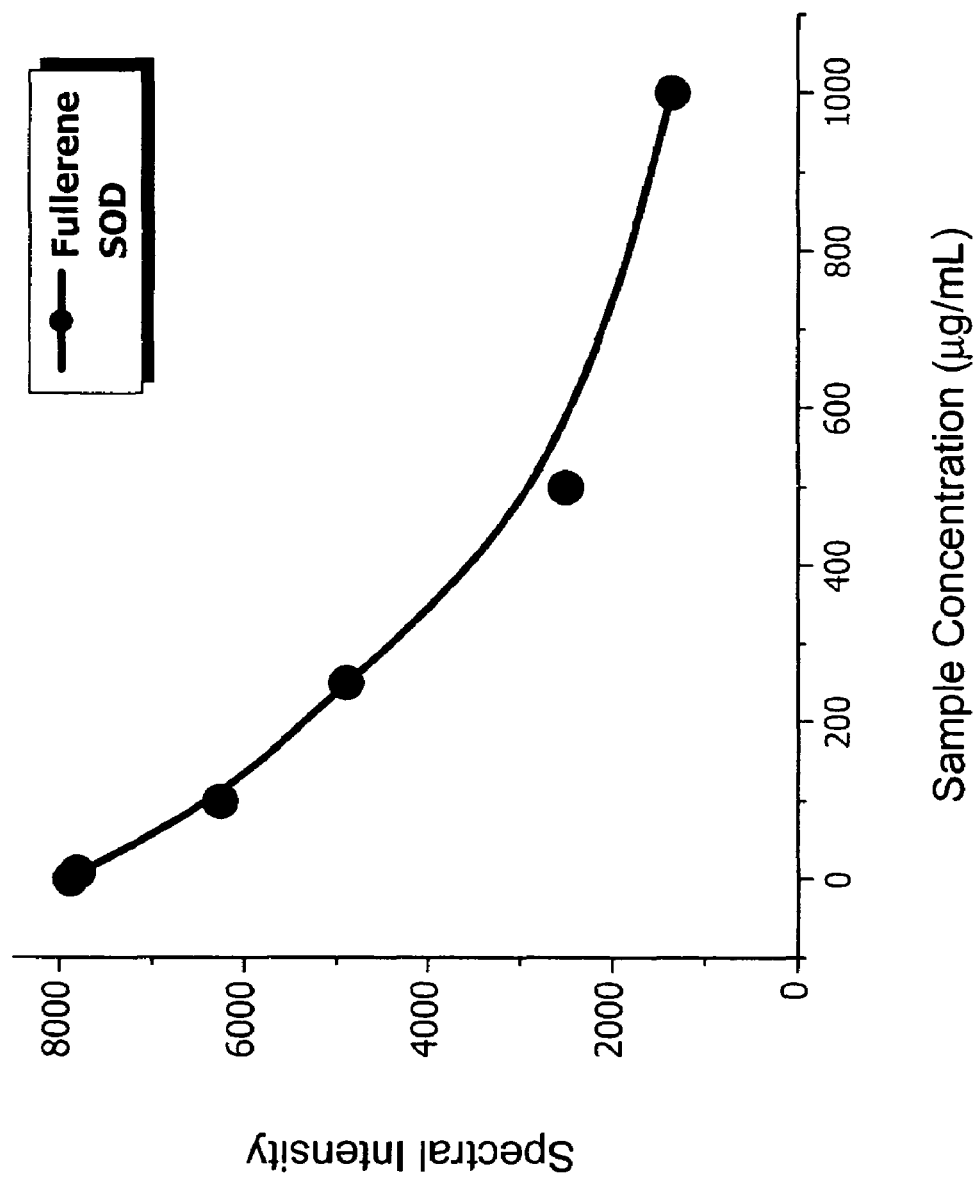
FIG. 3 is a graph wherein active oxygen-quenching ability is plotted with regard to the concentration of fullerene in an aqueous solution of the fullerene composite of this invention.

FIG. 3 shows results of plotting of active hydrogen-trapping ability with respect to fullerene concentration. It was known from these results that $IC_{50\ fullerene}$=361.76 μg/ml.

Figure 4:
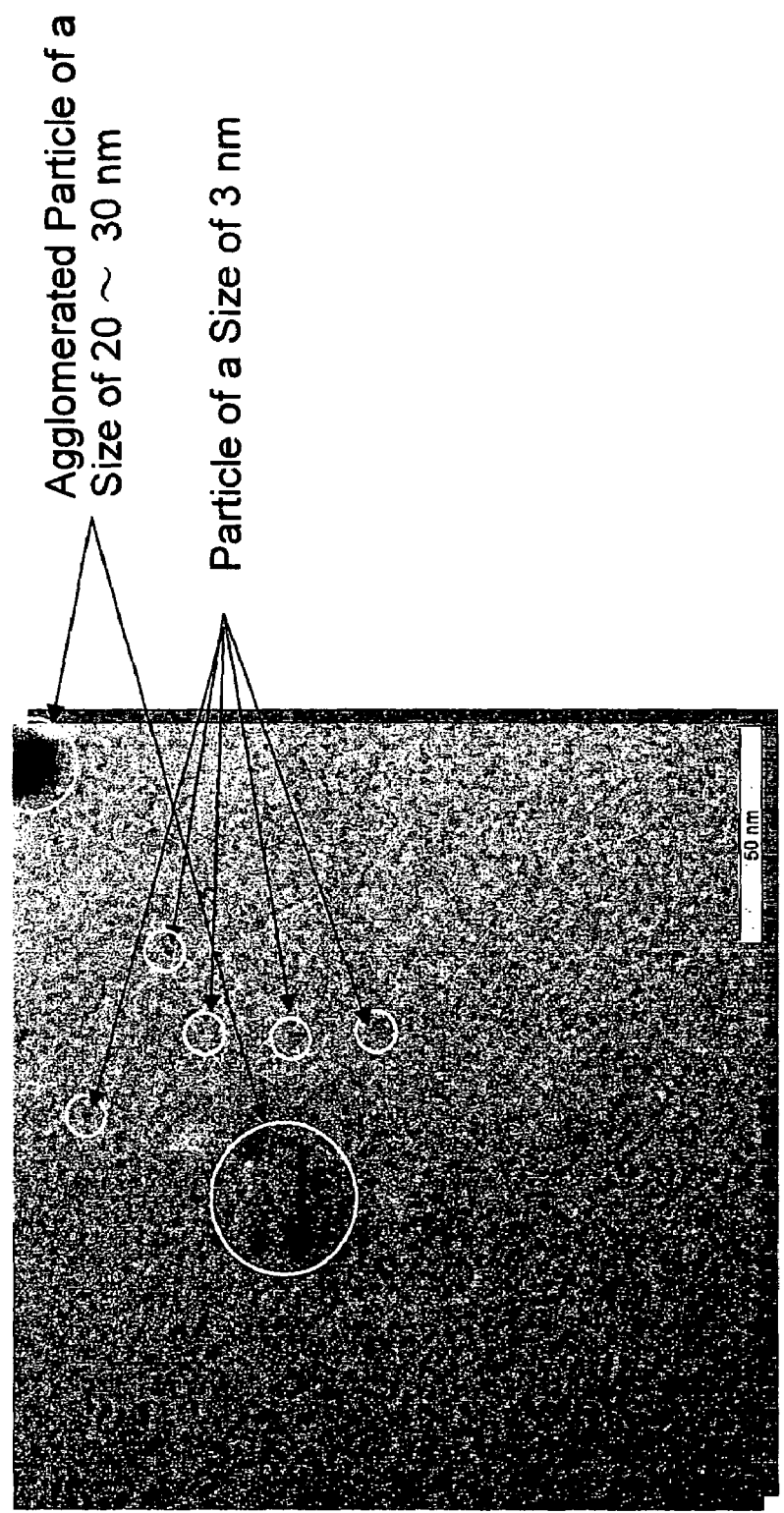
FIG. 4 is a photograph in place of drawing which shows the results of transmission electron microscope (TEM) observation of Gd-encapsulating fullerene composite of this invention.

Production of Composite of Gadolinium-encapsulating Fullerene and Acetal-PEG-PMAMA Block Copolymer and Measurement of Water Relaxation Time Gd-encapsulating $C_{82}$ fullerene ($Gd@C_{82}$) in an amount of 1 mg was mixed with 10 mg of DMF, and the resulting mixture was sonicated for three hours. Thereafter, acetal-PEG-PMAMA block copolymer (PEG/PMAMA=5,000/5,900) was added, so that the concentration of block copolymer might be 5 mg/ml with regard to DMF, and, then, the resulting solution was sonicated for one hour. Subsequently, the solution was put in a bag made of dialysis membrane with a molecular weight cut off of 12000 to 14000 which had been swollen with distilled water overnight, and was thus dialyzed against 2 l of distilled water (water was replaced three times, i.e., after 2, 5 and 10 hours; recovered after 24 hours). FIG. 4 is a photograph in place of drawing, which shows results of observation of thus prepared sample by transmission electron microscope (TEM).

There were dissolved a) thus prepared composite of $Gd@C_{82}$/block copolymer and b) $C_{60}$/block copolymer each in a mixed solvent of $H_2O:D_2O$=50:50 to give samples. The fullerene concentration of sample a) and the fullerene concentration of sample b), which were calculated from the absorbance of UV-Vis spectrum, were a) $23.36\times10^{-3}$ mM and b) $31.93\times10^{-3}$ mM.

With respect to the measurement of relaxation time ($T_1$ measurement), null point was firstly obtained by the null method, and, then, $T_1$ was guessed from thus obtained value, and, thus, each of conditions was set for measurement.

The index which shows a relaxation time-shortening effect is relaxivity (R). When C (mmol/l) defines the concentration of contrast medium, $T_{10}$ denotes longitudinal relaxation time before the administration of contrast medium (i.e., longitudinal relaxation time of solvent) and $T_{1p}$ denotes longitudinal relaxation time after the administration of contrast medium (i.e., relaxation time in the presence of sample), R is defined by the following formula:

$$R_1 = \frac{\frac{1}{T_{1p}} - \frac{1}{T_{10}}}{C}$$

In the above formula, $1/T_1$ which is the reciprocal of relaxation time is called relaxation rate, which is an index to show the rate of relaxation as it is named. Relaxivity (R), on the other hand, indicates how much the relaxation rate would increase when contrast medium spreads throughout the tissue up to a unit concentration. In other words, it means that, the larger R is, the higher is the relaxation rate-increasing effect (relaxation time-shortening effect) of contrast medium.

Relaxivity R was calculated on the basis of the concentration and $T_1$ of samples, and from the relaxation time of solvent used, and, thus, comparison was made. Results are shown in Table 1. It is seen in Table 1 that $Gd@C_{82}$/polymer composite has a significantly high R value, and is promising as a contrast medium for MRI.

TABLE 1

| Sample | $T_1$ (second) | $R_1$ |
| --- | --- | --- |
| $Gd@C_{82}$/polymer | 2.726 | 13.36 |
| $C_{60}$/polymer | 4.402 | 5.4 |
| $D_2O + H_2O$ | 18.271 | 0 |

INDUSTRIAL APPLICABILITY

The finely particulate composite of fullerene with block copolymer, of carbon nanotube with block copolymer, and of metal-encapsulating fullerene with block copolymer are capable of solubilizing fullerene in water, and are therefore able to broaden the range of use of fullerene in such a field as medicinal drugs, diagnostic drugs, etc. Hence, this invention is usable for the manufacture of medicines or the like.

The invention claimed is:

1. A finely particulate composite comprising a carbon compound of closed-shell structure which essentially consists of 30 to 2000 carbon atoms and a block copolymer, wherein said carbon compound is covered with polymer chains of the block copolymer and is encapsulated in a polymer micelle which is originated in the block copolymer having a polymer chain segment containing a recurring unit which has, on its side chain, a tertiary amino group and/or a secondary amino group and a poly(ethyleneglycol) chain segment, and which has the former segment as a core and the latter segment as a shell.

2. A finely particulate composite of claim 1 which has a solubility of 0.5 mg/ml or more in distilled water at 25° C.

3. A finely particulate composite of claim 1 wherein the polymer chain segment containing a recurring unit which has, on its side chain, a tertiary amino group and/or a secondary amino group is originated from a monomer of general formula (A) as follows:

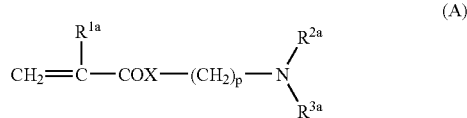

wherein $R^{1a}$ denotes a hydrogen atom or a $C_{1-6}$ alkyl group, $R^{2a}$ and $R^{3a}$ either, independently, denote a $C_{1-6}$ alkyl group or, taken together, may form, with the nitrogen atom to which they are bound, a five- or six-membered heterocycle which may contain further one or two nitrogen atoms, an oxygen atom or a sulfur atom, X denotes —O— or —NH—, and p denotes an integer of 2 to 6, said finely particulate composite having a solubility of 0.5 mg/ml or more in distilled water at 25° C.

4. A finely particulate composite of claim 1 wherein the block copolymer has general formula (A-1) as follows:

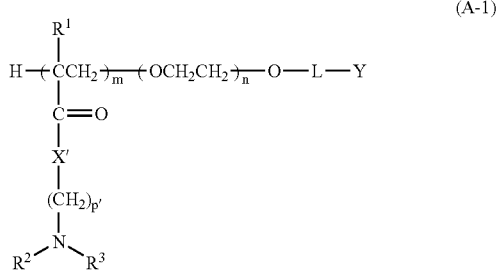

wherein $R^1$ denotes a hydrogen atom or a $C_{1-6}$ alkyl group, $R^2$ and $R^3$ either, independently, denote a $C_{1-6}$ alkyl group or, taken together, may form, with the nitrogen atom to which they are bound, a five- or six-membered heterocycle which may contain further one or two nitrogen atoms, an oxygen atom or a sulfur atom, X' denotes —O— or —NH—, L denotes a $C_{1-6}$ alkylene or a valence bond, Y denotes a hydrogen atom, a hydroxyl group, a carboxyl group, an amino group, an acetalized formyl group or a formyl (or aldehyde) group, m denotes an integer of 1 to 10,000, n denotes an integer of 10 to 20,000, and p' denotes an integer of 2 to 6.

5. A finely particulate composite of claim 1 wherein the carbon compound is $C_{30}$-$C_{120}$ fullerene which consists of carbon atoms alone.

6. A process to produce a finely particulate composite of claim 1, wherein a carbon compound of closed-shell structure which essentially consists of 30 to 2000 carbon atoms and a block copolymer having a polymer chain segment containing a recurring unit which has, on its side chain, a tertiary amino group and/or a secondary amino group and a poly(ethyleneglycol) chain segment are dissolved in a dipolar aprotic solvent and mixed, and that the resulting mixture is dialyzed against an aqueous solvent through a dialysis membrane whose molecular weight cut off is 12000 to 14000, to give a finely particulate composite wherein said carbon compound is encapsulated in a structure originated in the block copolymer.

7. An active oxygen scavenger which contains a finely particulate composite of claim 1 as an effective ingredient.

8. An active oxygen scavenger of claim 7 which is used in a field of foods, medical treatment, dermatology or cosmetics.

9. A finely particulate composite comprising a carbon compound of closed-shell structure which essentially consists of 30 to 2000 carbon atoms and a block copolymer, wherein said carbon compound is covered with polymer chains of the block copolymer and is encapsulated in a polymer micelle which is originated in the block copolymer having a polymer chain segment containing a recurring unit which has, on its side chain, a tertiary amino group and/or a secondary amino group and a poly(ethyleneglycol) chain segment, and which has the former segment as a core and the latter segment as a shell, and wherein an ultrafine particle of metal either in the form of metal element or in the form of its ion is encapsulated in the closed-shell structure of said carbon compound.

10. A finely particulate composite of claim 9 wherein the metal either in the form of metal element or in the form of its ion is paramagnetic metal.

11. A finely particulate composite of claim 10 wherein the paramagnetic metal is originated in an element selected from the group consisting of gadolinium, europium, terbium and erbium.

12. A contrast medium which comprises a finely particulate composite of claim 11 as an effective ingredient.

13. A finely particulate composite of claim 9 wherein the polymer chain segment containing a recurring unit which has, on its side chain, a tertiary amino group and/or a secondary amino group is originated from a monomer of general formula (A) as follows:

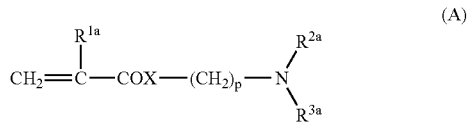

wherein $R^{1a}$ denotes a hydrogen atom or a $C_{1-6}$ alkyl group, $R^{2a}$ and $R^{3a}$ either, independently, bound, a five- or six-membered heterocycle which may contain further one or two nitrogen atoms, an oxygen atom or a sulfur atom, X denotes —O— or —NH—, and p denotes an integer of 2 to 6.

14. A finely particulate composite of claim 13 wherein the block copolymer has general formula (A-1) as follows:

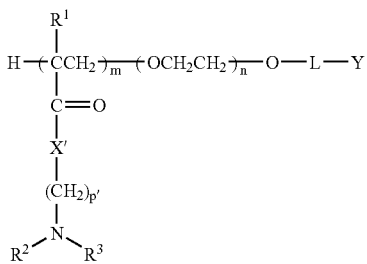

(A-1)

wherein $R^1$ denotes a hydrogen atom or a $C_{1-6}$ alkyl group, $R^2$ and $R^3$ either, independently, denote a $C_{1-6}$ alkyl group or, taken together, may form, with the nitrogen atom to which they are bound, a five- or six-membered heterocycle which may contain further one or two nitrogen atoms, an oxygen atom or a sulfur atom, X' denotes —O— or —NH—, L denotes a $C_{1-6}$ alkylene or a valence bond, Y denotes a hydrogen atom, a hydroxyl group, a carboxyl group, an amino group, an acetalized formyl group or a formyl (or aldehyde) group, m denotes an integer of 1 to 10,000, n denotes an integer of 10 to 20,000, and p' denotes an integer of 2 to 6.

15. A contrast medium which comprises a finely particulate composite of claim 13 as an effective ingredient.

* * * * *